United States Patent [19]

Oertel, III et al.

[11] Patent Number: 4,522,762

[45] Date of Patent: Jun. 11, 1985

[54] DIISOCYANATE

[75] Inventors: Richard W. Oertel, III, Guilford; Reinhard H. Richter, North Haven; Benjamin W. Tucker, Bethany, all of Conn.

[73] Assignee: The Upjohn Company, Kalamazoo, Mich.

[21] Appl. No.: 440,565

[22] Filed: Nov. 10, 1982

[51] Int. Cl.³ .................... C07C 69/00; C08G 18/10
[52] U.S. Cl. .................. 260/453 A; 528/65; 528/66
[58] Field of Search .................... 260/453 A

[56] References Cited

U.S. PATENT DOCUMENTS

| | | | |
|---|---|---|---|
| 2,723,265 | 11/1955 | Stallman | 260/453 A X |
| 3,515,740 | 6/1970 | Frampton et al. | 260/464 |
| 3,584,045 | 6/1971 | Feldman et al. | 260/453 A |
| 3,624,122 | 11/1971 | Kamal et al. | 260/453 A |
| 3,625,986 | 12/1971 | Feldman et al. | 260/453 A |
| 3,787,469 | 1/1974 | Davis et al. | 260/453 A |
| 4,113,705 | 9/1978 | Bock et al. | 260/859 R |

OTHER PUBLICATIONS

Liberman et al., Doklady Akademii Nauk SSSR, vol. 201, No. 1, pp. 115–116, (1971).

*Primary Examiner*—Alan Siegel
*Attorney, Agent, or Firm*—James S. Rose; Denis A. Firth

[57] ABSTRACT

A novel aliphatic diisocyanate, namely 1,4-bis(2-isocyanatoethyl)cyclohexane, is disclosed. Polyurethanes derived from this diisocyanate exhibit advantageous properties. Illustratively, polyurethane elastomers prepared from the above diisocyanate, a polymeric diol and a low molecular weight diol extender, possess significantly improved resilience properties and are useful in the preparation of automobile bumpers, fenders and the like.

1 Claim, No Drawings

DIISOCYANATE

BACKGROUND OF THE INVENTION

1. Field of the Invention

This invention relates to novel isocyanates and is more particularly concerned with novel aliphatic isocyanates and with methods for their preparation and with polyurethanes prepared therefrom by reaction with active-hydrogen containing materials.

2. Description of the Prior Art

A wide variety is known of cyclohexanes substituted by isocyanatoalkyl substituents. Illustratively U.S. Pat. No. 3,787,469 discloses 1,4-bis(isocyanatomethyl)-cyclohexane; U.S. Pat. No. 3,625,986 discloses 1(isocyanatomethyl)-1-(3-isocyanatopropyl)cyclohexane (see also U.S. Pat. Nos. 3,584,045 and 3,515,740) and 1-(isocyanatomethyl)-1-(2-isocyanato-ethyl)cyclohexane; U.S. Pat. No. 3,624,122 discloses 1-alkyl-2-isocyanatomethyl-4-isocyanatoalkylcyclohexanes; and U.S. Pat. No. 4,113,705 shows 1-(2-isocyanatoethyl)-4-(isocyanatomethyl)-4-(3-isocyanatopropyl)cyclohexane. To the best of applicants' knowledge the compound 1,4-bis(2-isocyanato-ethyl)cyclohexane has not been described previously. It has now been found that this latter diisocyanate can be prepared readily in high yield and that it can be utilized to prepare polyurethanes which possess highly advantageous properties.

SUMMARY OF THE INVENTION

This invention comprises a novel aliphatic diisocyanate, namely, 1,4-bis(2-isocyanatoethyl)cyclohexane (I), and polyurethanes derived therefrom by reaction with active hydrogen-containing compounds in accordance with processes well-known in the art.

DETAILED DESCRIPTION OF THE INVENTION

The novel aliphatic diisocyanate of the invention is prepared conveniently from the known compound 1,4-bis(hydroxymethyl)cyclohexane by the combination of steps shown schematically as follows:

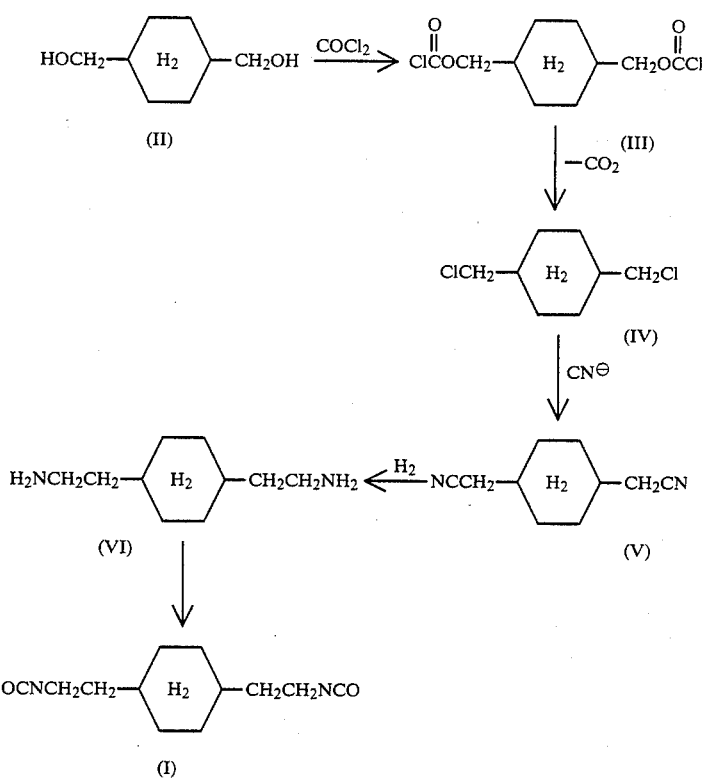

In accordance with the above reaction scheme the starting diol (II) is reacted with phosgene, advantageously in the presence of an inert organic solvent, to form the corresponding bis(chloroformate) using procedures well-known in the art; see, for example, S. Petersen, in Houben-Weyl, Methoden der Organischen Chemie, Vol. VIII, Part 3, p. 101, Georg Thieme Verlag, Stuttgart, 1952.

The term "inert organic solvent" means organic solvents which do not enter into reaction with any of the reactants employed in the process or interfere in any other way with the desired course of the reaction. Illustrative of inert organic solvents are chloroform, dichloroethane, benzene, toluene, chlorobenzene and the like. The phosgenation is generally conducted at temperatures which, advantageously, are in the range of about 10° C. to about 120° C., and preferably in the range of about 60° C. to about 90° C. The progress of the reaction can be followed by conventional analytical techniques such as infrared spectroscopy and the like. When the reaction is judged to be complete the bis(chloroformate) (III) can, if desired, be isolated from the reaction mixture, for example, by removing the inert organic solvent and any excess phosgene by distillation. However, it is generally unnecessary to isolate the bis(chloroformate) (III) since it is found that the reaction product from the first step can, after purging any excess phosgene therefrom, be used as such in the next step of the process.

In the second step of the process the bis(chloroformate), advantageously in the form of the reaction mixture obtained in the first step, is heated in the presence of a catalytic amount of an N,N-disubstituted-formamide such as dimethylformamide, diethylformamide and the like using the process for the preparation of aliphatic hydrocarbyl chlorides which is described in the application of Reinhard H. Richter et al which is being filed on an even date herewith. The reaction is conducted at a temperature in the range of about 40° C. to about 150° C. and preferably in the range of about 60° C. to about 100° C. and the decarboxylation of the bis(chloroformate) (III) to the corresponding 1,4-bis(chloromethyl)cyclohexane (IV) proceeds smoothly and in high yield. The progress of the reaction can be followed by routine analytical procedures such as infrared spectroscopic analysis or by measuring the amount of carbon dioxide eliminated from the reaction mixture. The compound (IV) can be isolated from the reaction mixture by any convenient means, if so desired. For example, the inert organic solvent and the N,N-disubstitutedformamide catalyst can be removed by distillation and the compound (IV) can, if desired, be purified by distillation under reduced pressure or by chromatography or like means. Alternatively, for use in the next step of the process, the compound (IV) can be kept in solution in the reaction product and the N,N-disubstitutedformamide used as catalyst can be removed by distillation or by extraction with water before proceeding to the next step of the process.

The bis(chloromethyl)cyclohexane (IV) obtained as described above is then reacted in the presence of an inert organic solvent (the reaction solution derived from the previous step without isolation of the compound IV can be used) with an alkali metal cyanide such as sodium, potassium, lithium and the like cyanides using procedures well-known in the art, such as described by R. A. Smiley and C. Arnold, J. Org. Chem., 25, 257, (1960) and L. Friedman and H. Shechter, J. Org. Chem., 25, 877, (1960). The reaction is conducted at temperatures in the range of about 70° C. to about 180° C. and preferably about 80° C. to about 140° C. Advantageously, the alkali metal cyanide is added portionwise, with vigorous agitation, in the solid state to the solution of dichloride (IV) in the inert organic solvent. The reactants are employed in at least stoichiometric proportions and advantageously with the alkali metal cyanide present in slight excess over the stoichiometric amount. The reaction proceeds smoothly and gives the desired dinitrile (V) in high yield. The resulting reaction product is a mixture of alkali metal chloride (as a precipitate) and a solution of the dinitrile (V) in inert organic solvent. The alkali metal chloride is removed by filtration, centrifugation and the like and the dinitrile (V) is isolated readily by evaporation of the solvent. The dinitrile (V) can be purified, if desired, by conventional techniques such as crystallization, before being subjected to the next step in the process of the invention.

The dinitrile (V) is then hydrogenated to the corresponding diamine (VI) using any of the procedures known in the art for the reduction of a nitrile to the corresponding amine; see, for example, Chemistry of Carbon Compounds, edited by E. H. Rodd, Volume IIIA, p. 488, Elsevier, New York, 1954. Such techniques include reduction using sodium in the presence of a lower aliphatic alcohol such as methanol, ethanol, and the like as well as hydrogenation in the presence of a catalyst such as supported platinum and palladium catalysts, Raney nickel and the like. The diamine (VI) so obtained can be purified, if desired, by conventional procedures; for example, the diamine can be converted to its salt with a mineral or organic acid and the salt can be purified by recrystallization before being converted back to the free diamine by reaction with the appropriate base such as an alkali metal hydroxide.

In the final step of the process the diamine (VI) is converted to the desired diisocyanate (I) by phosgenation using procedures well-known in the art. The phosgenation is carried out advantageously using procedures described by Siefken, Annalen, 562, 75 et seq., 1949. Illustratively, the diamine (VI) or an acid addition salt thereof such as the dihydrochloride, dihydrobromide, and the like, is treated with phosgene in the presence of an inert organic solvent such as benzene, toluene, anisole, xylene, naphthalene, decalin, chlorobenzene, dichlorobenzene, bromobenzene, chlorotoluene and the like. The reaction is conducted initially at ambient or below ambient temperatures such as about $-10°$ C. to about 20° C. and subsequently at elevated temperatures, preferably at temperatures of the order of 100° C. to 200° C. The phosgene is conveniently employed in approximately stoichiometric proportions but an excess of phosgene can be employed if desired. The resulting diisocyanate (I) is isolated from the reaction mixture by conventional procedures. For example, the excess phosgene is purged from the reaction mixture using a stream of nitrogen or other inert gas and the inert solvent is removed by distillation under reduced pressure. The residual diisocyanate (I) can be purified, if desired, by conventional procedures such as by distillation and the like.

The diisocyanate (I) is a colorless liquid. As will be readily apparent the diisocyanate (I) can exist in a number of stereoisomeric forms. While theoretically more than two stereoisomeric forms are possible, it is found in practice that the cyclohexane ring tends to assume the "chair" configuration rather than the "boat" configuration at least at room temperature and that, with the cyclohexane ring in the "chair" form, the two stereoisomers present in the diisocyanate (I) are the cis- and the trans-isomer. The above two isomers in the diisocyanate (I) can vary in proportion depending principally on the proportion of these isomers present in the starting diol (II) unless specific steps are taken to separate the two isomers or enhance the proportion of one isomer with respect to the other at some stage in the conversion of the starting diol (II) to the diisocyanate (I). If desired, the stereoisomers can be separated by known procedures, such as fractional crystallization or distillation or after derivatization, i.e. conversion of (VI) into a bis(imine) followed by fractional crystallization.

Thus, the diisocyanate (I) can be prepared in the form of the pure trans-isomer or the pure cis-isomer or a mixture of these two isomers in any proportion. Depending upon the particular use for which the diisocyanate (I) is to be employed it may be important to select a particular isomer or mixture of isomers as discussed in more detail below. However, it is to be understood that any and all such isomers and mixtures of isomers are included within the present invention.

The diisocyanate (I) can be employed in the preparation of polyurethanes, both cellular and non-cellular, which have hitherto been prepared from closely related aliphatic diisocyanates. In common with the known aliphatic isocyanates the diisocyanate (I) of the invention gives rise to polyurethanes which do not suffer discoloration on aging, i.e. do not give rise to the brown color which is a characteristic of aged polyurethanes prepared from aromatic polyisocyanates. This property makes the diisocyanate (I) advantageous in the preparation of polyurethanes for coating compositions which are water-white, transparent and resistant to color formation on aging. The diisocyanate (I) is also highly advantageous in the preparation of elastomers which are generally prepared by reaction with polymeric diols and low molecular weight extender diols in accordance with methods well-known in the art. It is found that the elastomers so prepared exhibit significantly improved resilience properties (as measured by ASTM-D2632 test for resilience) when compared with elastomers prepared in exactly the same manner using the next lower homologue, namely 1,4-bis(isocyanatomethyl)cyclohexane, of the diisocyanate (I); see the data set forth in Example 2 below. In this type of application the proportion of stereoisomers in the diisocyanate (I) plays a role. Thus the properties, particularly the resilience, of the elastomers in question is enhanced to the greatest extent when the pure trans-isomer is employed and, when a mixture of stereoisomers is used, the degree of enhancement of properties is substantially directly proportional to the proportion of trans-isomer present in the starting diisocyanate.

The following examples describe the manner and process of making and using the invention and set forth the best mode contemplated by the inventors of carrying out the invention but are not to be construed as limiting.

EXAMPLE 1

A. Preparation of 1,4-bis(chloromethyl)cyclohexane (IV)

A charge of 250 ml. of 1,2-dichloroethane was heated under reflux while a stream of phosgene was bubbled into the liquid and a total of 58 g. (0.4 mole) of 1,4-bis(hydroxymethyl)cyclohexane was added in small portions over a period of 1 hour, allowing the material added in each portion to dissolve before the next portion was added. Shortly after the addition was completed, the introduction of phosgene was terminated and the excess phosgene was purged from the reaction mixture using a stream of nitrogen. When the purging was complete, part of the dichloroethane solvent was removed by evaporation. To the concentrate was added 10 ml. (0.13 mole) of dimethylformamide and the resulting mixture was heated under reflux for approximately eight hours. At the end of this time the excess solvent and dimethylformamide were removed by distillation under low vacuum and the residue was distilled in vacuo to obtain 66.93 g. (92 percent theoretical yield) of 1,4-bis(chloromethyl)cyclohexane in the form of a colorless liquid having a boiling point of 65° to 70° C. at 0.1 mm. of mercury.

B. Preparation of 1,4-bis(cyanomethyl)cyclohexane (V).

A suspension of 70 g. (1.4 mole) of sodium cyanide in 200 ml. of dimethyl sulfoxide was heated with stirring to 90° C. and a total of 108.6 g. (0.6 mole) of 1,4-bis(chloromethyl)cyclohexane Ewas added over a period of approximately 1 hour. The temperature of the reaction mixture reached a maximum of 168° C. shortly after addition commenced but levelled off at 130°-132° C. towards the end of the addition. After the addition was complete, the resulting mixture was maintained at 115° C. with continuous stirring for a further 1.5 hr. and was then cooled to room temperature (circa 20° C.). The cooled mixture was filtered and the insoluble material was washed on the filter with dimethyl sulfoxide. The combined filtrate and washings were distilled to remove the major portion of the solvent and the undistilled residue was allowed to cool to room temperature whereupon it crystallized. The residue was dissolved in 200 ml. of toluene and the solution so obtained was extracted 5 times with 40 ml. portions of water to remove the last traces of dimethyl sulfoxide. The washed toluene solution was dried over anhydrous sodium sulfate and the toluene was then removed by distillation. The residue crystallized in the form of a honey-colored solid. There was thus obtained 92.5 g. (94 percent theoretical yield) of 1,4-bis(cyanomethyl)cyclohexane. The identity and purity of the product was confirmed by gel permeation chromatography and by infrared and nuclear magnetic resonance spectra.

C. Preparation of 1,4-bis(2-aminoethyl)cyclohexane (VI)

A total of 50 g. of 1,4-bis(cyanomethyl)cyclohexane (prepared as described above), 100 ml. of toluene, and 8 g. of Raney nickel (previously washed with methanol and toluene) was charged to a Parr bomb hydrogenation apparatus. The bomb was cooled in dry ice and pressured with anhydrous ammonia followed by hydrogen to a pressure of 800 psi. The bomb was then heated to 90°-100° C. at which point the pressure reached 1040 psi. After about 1 hour of heating the uptake of hydrogen began. When the pressure had fallen to 400 psi the bomb was charged with additional hydrogen to a pressure of 820 psi. The pressure fell to 500 psi over a period of 2.75 hours and the bomb was again repressured to 800 psi and hydrogenation was continued for a further 1 hour at the end of which time the pressure had fallen to 770 psi. The hydrogenation was then stopped and the reaction product was cooled to room temperature (circa 20° C.) and allowed to stand overnight. The reaction product was then filtered and the insoluble material was washed on the filter with toluene. The combined filtrate and washings were then distilled under reduced pressure to remove the toluene and the residue was distilled in vacuo to yield 48.8 g. (93 percent theoretical yield) of 1,4-bis(2-aminoethyl)cyclohexane (VI) in the form of an oil having a boiling point of 86°-92° C. at 0.1 mm. of mercury. This diamine was shown by C-13 nuclear magnetic resonance spectral analysis to contain the cis- to trans-isomers of (VI) in a ratio of approximately 1:2.5.

D. Preparation of 1,4-bis(2-isocyanatoethyl)cyclohexane (I)

A total of 160 g. (1.62 mole) of phosgene was dissolved in 400 ml. of anisole maintained in a cooling bath at 8°-10° C. The resulting solution was maintained at the same temperature and stirred while a solution of 48 g. (0.28 mole) of 1,4-bis(2-aminoethyl)cyclohexane (prepared as described above) in 275 ml. of anisole was added dropwise under an atmosphere of nitrogen. The addition took place in 1 hour and 10 minutes. After the addition was complete, the resulting mixture was heated gradually to 112°-115° C. and finally to a temperature of 131 to 135° C. over a total time of 5 hours. During the heating period a stream of phosgene was bubbled through the reaction mixture. At the end of the heating period the reaction mixture was purged of excess phosgene using a stream of nitrogen and was then evaporated on a rotary evaporator to remove the bulk of the solvent. The remainder of the solvent was removed by distillation and the residue was distilled under reduced pressure to obtain 54.6 g. (87 percent theoretical yield) of 1,4-bis(2-isocyanatoethyl)cyclohexane in the form of an oil having a boiling point of 130°–133° C. at 0.1 mm. of mercury. The material was found to have an isocyanate equivalent of 113. The identity of the material was confirmed by the infrared spectrum and the nuclear magnetic resonance spectrum.

EXAMPLE 2

This example shows a direct comparison of two elastomers made under identical conditions and using the same reactants in the same proportions by equivalents, the sole difference being that in one case the isocyanate used was 1,4-bis(2-isocyanatoethyl)cyclohexane and, in the other case, was 1,4-bis(isocyanatomethyl)cyclohexane. The latter diisocyanate was prepared from the corresponding diamine (Eastman Kodak) by phosgenation using the same procedure as that described in Example 1, Part D. The starting diamine was found to have a ratio of content of cis- to trans-isomer of 1:3.3; i.e. the 1,4-bis(isocyanatomethyl)cyclohexane derived therefrom had a significantly greater trans-isomer content than the diisocyanate of Example 1 above.

The procedure employed to prepare both elastomers was as follows. The reactants and proportions (by equivalents or by weight where indicated) of each were:

|  | Proportion |
| --- | --- |
| Polytetramethylene glycol Eq. wt. = 488.7 (Teracol 1000:DuPont) | 1.0 equivs. |
| 1,4-butanediol | 2.25 equivs. |
| Diisocyanate | 3.25 × 1.02 (index) |
| Antioxidant (Irganox 1010) | 0.25% w/w* |
| Lubricant (Advawax 280) | 0.5% w/w* |
| Catalyst (50% solution of stannous octoate in dioctyl phthalate) | 0.025% w/w* |

*Proportions based on total weight of reactants.

The polytetramethylene glycol, 1,4-butanediol, antioxidant, catalyst and lubricant were mixed and the mixture was degassed by heating at 90° to 100° C. for 2 hours at a pressure of about 0.1 mm. of mercury. The diisocyanate was added to the degassed mixture with vigorous stirring and the mixed reactants were poured into a Teflon lined pan and reaction was allowed to proceed to completion. The resulting polyurethane was then granulated, dried at 90° C. for 4 hrs. and subjected to injection molding using a barrel temperature of 200° to 210° C. and a mold temperature of 50° C., to form test sheets ($4\frac{3}{4}'' \times 4\frac{3}{4}'' \times 1/16''$) for determination of physical properties. The physical properties so determined for the two elastomers were as follows.

|  | Elastomer from 1,4-bis(isocyanato-methyl)cyclohexane | Elastomer from diisocyanate of Example 1 |
| --- | --- | --- |
| Tensile strength: psi | 4700 | 2550[1] |
| Elongation at break: % | 630 | 840 |
| Hardness: Shore A | 93 | 91 |
| Clashberg Modulus $T_c$ | −64° C. | −66° C. |
| Bayshore rebound (ASTM-D2632) | 29 | 35 |
| Density g/cc | 1.094 | 1.084 |

Footnote:
[1]The test bars showed "necking", i.e. stretching at approximately the midpoint rather than uniformly throughout the bar.

The above results demonstrate that the elastomer prepared from the diisocyanate of Example 1 possessed significantly superior elongation and resiliency as compared with the elastomer from the prior art diisocyanate in spite of the higher trans-isomer content of the latter. The higher trans content would be expected to enhance the resiliency of the elastomer. The difference in resiliency as measured by the above test confirmed an observation made in a simple manual test in which it was observed that the elastomer prepared from the diisocyanate of Example 1 had a much "snappier" feel, i.e. upon flexing the test sheet of the elastomer the return to original configuration upon release was very rapid in the case of the elastomer prepared from the diisocyanate of Example 1 but much more sluggish in the case of the elastomer prepared from the prior art diisocyanate.

We claim:
1. 1,4-bis-(2-isocyanatoethyl)cyclohexane.

* * * * *